US00PP20200P3

(12) United States Plant Patent
Jeske et al.

(10) Patent No.: US PP20,200 P3
(45) Date of Patent: Aug. 4, 2009

(54) HOP PLANT NAMED 'APOLLO'

(50) Latin Name: *Humulus lupulus L*
Varietal Denomination: APOLLO

(75) Inventors: Roger D. Jeske, Yakima, WA (US); Joe Brulotte, Yakima, WA (US)

(73) Assignee: S.S. Steiner, Inc., New York, NY (US)

( * ) Notice: Subject to any disclaimer, the term of this patent is extended or adjusted under 35 U.S.C. 154(b) by 185 days.

(21) Appl. No.: 11/344,246

(22) Filed: Jan. 31, 2006

(65) Prior Publication Data

US 2006/0218684 P1 Sep. 28, 2006

(51) Int. Cl.
*A01H 5/00* (2006.01)

(52) U.S. Cl. ..... Plt./236

(58) Field of Classification Search ..... Plt./236
See application file for complete search history.

*Primary Examiner*—Susan B McCormick Ewoldt
(74) *Attorney, Agent, or Firm*—Hayes Soloway P.C.

(57) ABSTRACT

A new and distinct variety of hop, *Humulus lupulus L.,* named "APOLLO" is characterized by its exceptional high percentage of alpha acids, excellent storage stability of alpha acids, low CoH value for an alpha variety, and resistance to hop powdery mildew strains found in Washington. The new variety was cultivated as a result of a cross in 2000 at Golden Gate Roza Hop Ranches in Prosser, Wash., United States and has been asexually reproduced in Prosser, Wash., United States.

2 Drawing Sheets

BACKGROUND OF INVENTION

The flowers (cones) of the female hop plant, *Humulus lupulus L,* are used in the making of beverages, especially beer, as a flavoring and processing component. Hops contribute towards the bitterness and aroma in beer as well as foam quality and flavor and taste stability.

Hop plants, hops cones, male hop flowers, hop plant parts, hop tissue cultures and hop extracts also have bioactive properties; including anti-microbial, anti-cancer, anti-osteoporosis, anti-oxidative, anti-inflammatory, antibiotic, soporific, anti-androgenic, and pro-estrogenic activities, among others; which may be used in herbal remedies, in antimicrobial preparations for food, fodder, food fermentation, food process, animal husbandry; or in non-food uses, such as composting, biofuel processing, fermentation process, water treatment, animal bedding and phytoremediation; and uses in cosmetics, in nutraceutical and in pharmaceutical applications and in research thereof. Examples activities and non-berverage uses are included herein by references: J Hazard Mater. Apr 26;91(1–3):95–112; Mol Cancer Ther. Sep; 1(11):959–69; Phytochemistry. May;65(10):1317–30; U.S. Pat. No 6,423,317 (2002); U.S. Pat. No. 6,623,775 (2003).

Agricultural end-product users, growers, handlers and processors of hops, of hop plants, of hop tissues and of hop products use hops and are affected by the agronomic, developmental, morphological, chemical and physical properties that vary among unique and distinct asexually reproduced varieties. This invention relates to an asexually produced hop variety, named "APOLLO", invented in a planned and systematically executed breeding program.

SUMMARY OF INVENTION

This invention relates to a new genetically, chemically, and morphologically distinct variety of hop selected from among the multitude of hop plants resulting from a controlled cross-pollination during the summer of 2000. The cross-pollination was between a proprietary female hop plant referred to as "Zeus" (non-patented) with a proprietary non-patented male hop plant (98001 X USDA 19058m)m. The parents of "98001" (non-patented) are female hop plant "Galena" (non-patented) and a male progeny of open pollinated "Nugget" (non-patented).

The cross-pollination resulting in "APOLLO" was performed in 2000 by Roger Jeske, one of the named inventors in a field in Prosser, Wash. During 2001 seeds collected from the cross-pollination were germinated and screened for powdery mildew resistance in a greenhouse in Prosser, Wash. These seedlings were planted in a field nursery and further screened for gender, vigor, cone type, and disease resistance with the best genotypes being advanced to a single hill hop nursery during the spring of 2002. Mr. Jeske discovered the "APOLLO" variety during the summer of 2002 among the numerous hop genotypes growing in a single hill hop nursery in Prosser, Wash. These hop genotypes growing in the single hill hop nursery were grown in a 3.5'×14' spacing on twine attached to an 18' trellis system.

Chemical analysis and field observations in 2002 demonstrated the "APOLLO" hop plant had unusually high percentage of alpha-acids (20–21%), lack of powdery mildew in the leaves and cones, low CoH value (25–26%) and an exceptional cone set. Cones were very dense, compact, and had high densities of lupulin glands. Vigor was average and yield potential appeared to be very good as the plant exhibited a columnar growth habit that was evenly distributed with cones from the trellis top to within 2 feet of the ground.

In 2003, "APOLLO" was asexually propagated in greenhouses at Prosser, Wash. Rhizomes from the original single hill plant of "APOLLO" were dug, divided and planted into multiple greenhouse grown containers. Softwood cuttings were periodically taken from these original containers until approximately 4,000 softwood-cutting plants were made. These plants constituted the first asexual reproduction of the "APOLLO" variety and represent the second generation. During 2003, these second generation plants were grown at two distinct geographical locations with no powdery mildew observed, even though powdery mildew was prevalent in the surrounding hop varieties. These two small scale trials consisted of a multi-hill planting (7 plants) located in fields in Prosser, Wash. and a multi-hill planting (7 plants) in fields located near Sunnyside, Wash. These trials were subjected to standard agronomic, cultural and management practices for the purpose of determining harvest ability, yield, chemical characteristic, and process ability. Also, established in 2003 was a large-scale trial of second-generation plants north of Prosser, Wash. This consisted of planting two acres in a 3.5'× 14' configuration (1778 hills), with two softwood cuttings of "APOLLO" planted per hill.

During 2003, 2004, and 2005 second-generation plants in the two small-scale trials and one large-scale trial in fields located in Prosser, Wash. were sampled for chemical analysis and harvested for yield evaluations. Results from the test plots provided additional information supporting the disease resistance, yield potential, and alpha-acids projections made from the original "APOLLO" plant (first generation) selected in 2002. This confirmed the exceptionally high yield and high alpha-acids percentages of the new variety. Greenhouse potted plants of second generation "APOLLO" that were grown in the two-acre test plot north of Prosser, Wash. were not harvested as babies in 2003, but sampling for alpha-acids confirmed the 20–21% values seen in 2002. The 2004 and 2005 commercially harvested two-acre test plot of second-generation "APOLLO" produced an average of 3000 lbs./acre. Commercially harvested hop cones were kiln dried to approximately 10% moisture, then were pressed into 200 lb. bales. Bale samples from the 2004–2005 second generation "APOLLO" hops grown in the Prosser, Wash. location showed an average alpha-acids level of 20.5% and beta-acids level of 6.2% (American Society of Brewing Chemists spectrophotometric method). The two acre plot of "APOLLO" produced >600 lbs./acre of alpha during both years. The highest producing commercial variety is "Zeus" (non-patented) (mother of "APOLLO") that routinely produces in excess of 500 lbs./acre of alpha, but seldom approaches the 600 lbs./acre level of alpha production. Storage stability of second generation "APOLLO" had an average (2003 and 2004) loss of alpha-acids of the harvested hop cones stored at room temperature (22° C.) for six months of 15%. This is comparable to the most stable commercial high alpha hop "Nugget" (non-patented).

In 2005, the second asexual reproduction of the "APOLLO" variety took place. The second-generation rootstock from the two acres was dug, divided and planted into two larger acreage test plots near Prosser, Wash. and near Sunnyside, Wash. These third generation plants were grown utilizing standard agricultural practices that are common for hop production, except no powdery mildew fungicides application was made. Third generation plants in both locations were sampled for chemical analysis and harvested for yield evaluations. Results from these third generation large-scale test plots provided additional information supporting the powdery mildew resistance and high alpha-acids percentages. The 2005 yield from these baby "APOLLO" plants was very good as compared to the baby yield of other commercial varieties (approximately 2000 lbs./acre).

Based on agronomic and chemical evaluations over a number of growing seasons both secondary and tertiary clones (second and third generations) of "APOLLO" exhibited genetic stability with respect to its novel characteristics. Including complete powdery mildew resistance to powdery mildew strains currently in the Yakima Valley, Wash., very high yield (>2800 lb./ac), exceptionally high alpha-acids percentages (>20%), low CoH values (25–27%), and excellent alpha acids stability during storage.

All observations, evaluations and testing of the "APOLLO" variety's agronomic, morphological, physical, and chemical properties were carried out by or directed by the inventors.

The variety "APOLLO" is mid maturing and is usually ready to pick between the 5th to the 20th of September. The very compact and ovoid shape cones of this variety are mid sized (200–250 mg.) and very plentiful resulting in easy mechanical picking and cleaning. The cones detach easily from stems, and the cones do not shatter during commercial harvesting and drying.

In order to demonstrate genetic and phenotypic distinctiveness to closely related varieties, "APOLLO" is compared to its mother and to other agronomically important varieties. "Zeus" (non-patented) is the parent of "APOLLO" and therefore similarities would be expected. The primary differences between the new "APOLLO" variety and "Zeus" is the complete resistance of "APOLLO" to the powdery mildew strains found in the Yakima Valley, higher alpha-acid percentages, a much better storage stability of alpha acids, and a lower CoH value as compared to "Zeus". Similarities include main vine inter-node lengths averaging 20 cm., which is 5–8 cm. shorter than most commercial hop varieties. Also, both varieties have five lobed main vine leaves, a columnar to fusiform growth habit and excellent production (>2800 lbs./acre). Chemical similarities show that both have an alpha/beta ratio of 3.0–3.5 and a humulene/caryophyllene ratio of 1.7–1.9

The detailed botanical description and drawings herein below allow distinction of the variety from related varieties. For illustration, comparisons of select distinguishing traits to further selected commercial varieties are set forth in Table 1.

TABLE 1

| | "APOLLO" | "Galena" | "Nugget" | "Zeus" |
|---|---|---|---|---|
| Alpha acids % w/w | 15-19 | 10-13.5 | 11-14 | 12-16.5 |
| Beta acids % w/w | 5.5-8.0 | 7.0-9.0 | 4.0-6.0 | 4.0-6.0 |
| CoH % w/w of alpha acids | 24-28 | 35-40 | 24-30 | 27-35 |
| Total Oil ml/100 g | 1.5-2.5 | 0.9-1.2 | 1.5-3.0 | 1.0-2.0 |
| Humulene % | 20-35 | 10-15 | 12-22 | 10-25 |
| Caryophyllene % | 14-20 | 3.0-5.0 | 7-10 | 5.0-15 |
| Powdery Mildew Disease | Resistant | Susceptible | Resistant | Susceptible |
| Cone Yield lbs/acre | 2800-3200 | 1600-2220 | 1700-2200 | 2400-3000 |

BRIEF DESCRIPTION OF THE DRAWINGS

The accompanying photographs illustrate the cones, leaves and growth habit of the new "APOLLO" variety.

GENERAL BOTANICAL DESCRIPTION OF THE VARIETY

Figure 1:
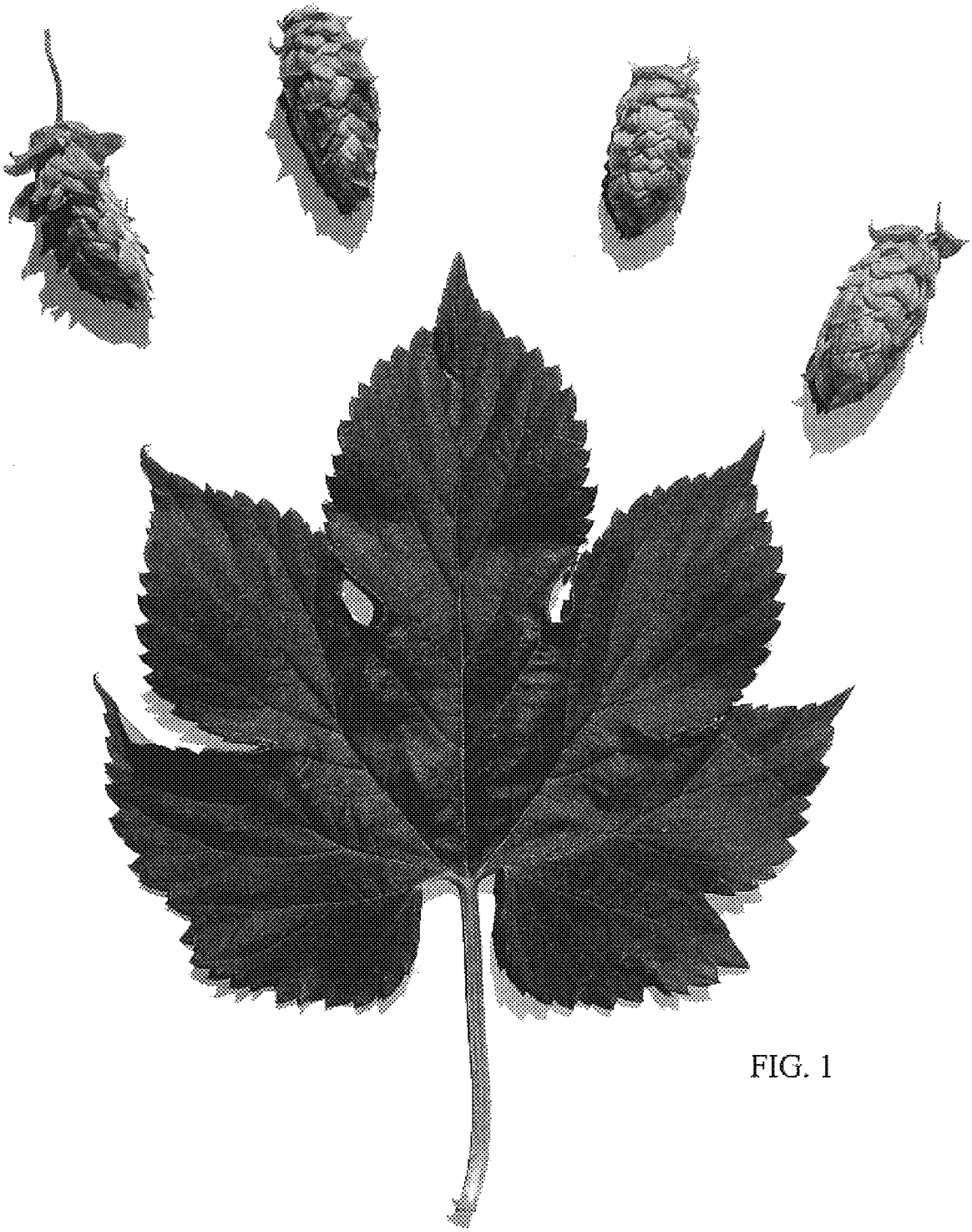
FIG. 1 depicts a close up of whole cones and a mature main vine leaf.
Figure 2:
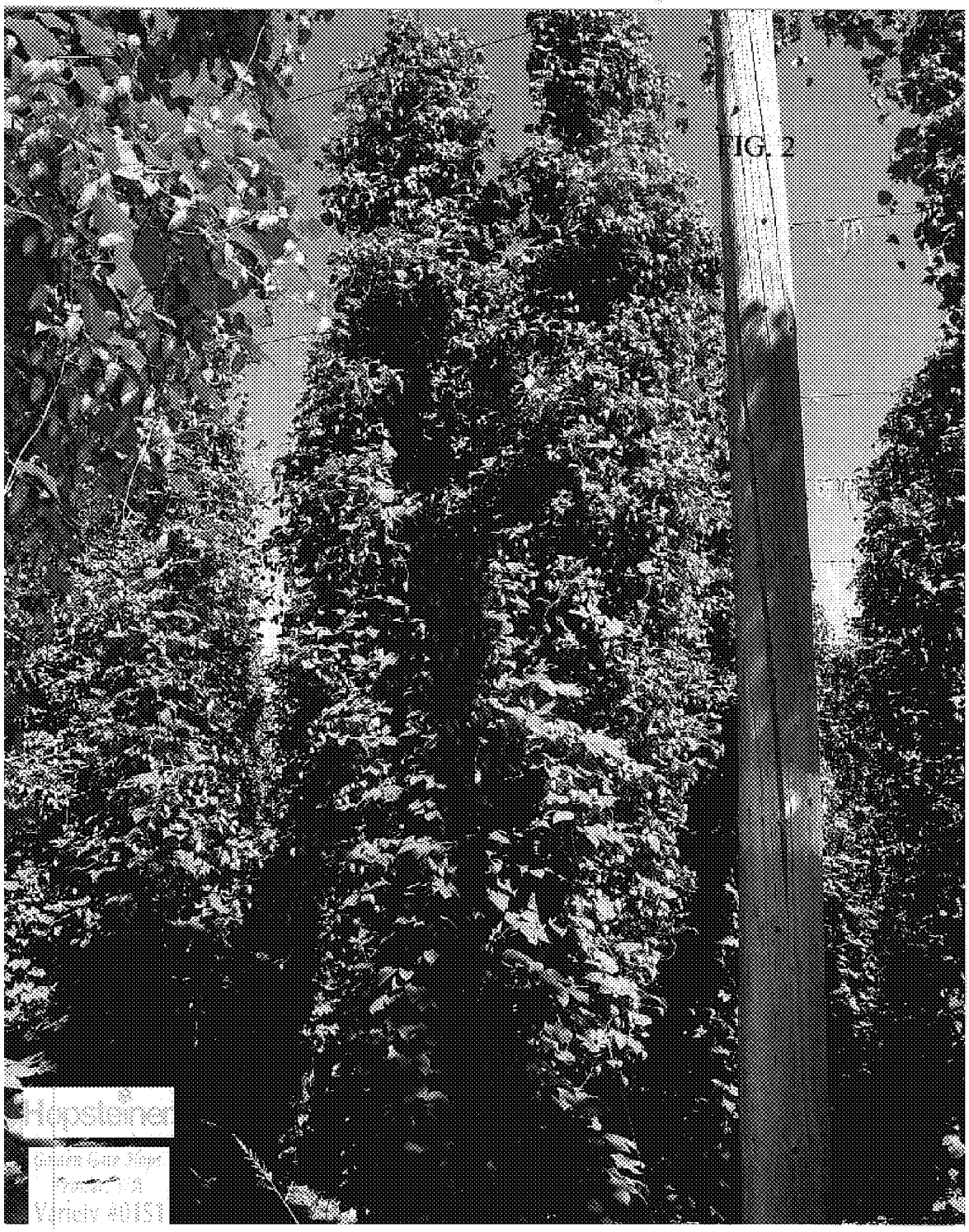
FIG. 2 depicts the appearance of the plants and cones as they are growing in the field on high trellis (18') approaching harvest time.

This description provides information on agronomic, morphological, chemical and processing characteristics of the new variety that are used in distinction and identification of a new hop variety and its parts and products by practitioners of the industries that use hops as described herein above.

General information on the botanical characteristics and cultural aspects of hop plants as they relate to agronomics, breeding and food use are particularly well discussed in the prior art, especially, U.S. Pat. Nos. PP10,956 and PP13,132 and the literature; "Steiner's Guide to American Hops Book III", 1986; "Hops" Published by Chapman and Hall, 1991. Detailed botanical information below of the present variety is directly comparable to the prior art, as contained by reference herein.

DETAILED BOTANICAL DESCRIPTION OF THE VARIETY

Following is a detailed description of the botanical and analytical chemical characteristics of the new variety. The information for this botanical description was either collected or verified during the growing seasons of 2002 through 2005 in the growing areas north of Prosser, Wash. and south of Sunnyside, Wash. Botanical characteristics, and to a lesser degree the analytical characteristics are somewhat dependent on cultural practices and climatic conditions and can vary with location or year:

1. Parentage: A hop plant originating from a controlled cross-pollination between proprietary non-patented female hop plant referred to as "Zeus" with a proprietary non-patented male hop plant (98001 X USDA 19058m)m.
2. Locality where grown and observed: North of Prosser, Wash. and south of Sunnyside, Wash.
3. Agronomic factors: "APOLLO" exhibits moderate growth rates. Dates of first and last harvest are approximately September 5 and September 20. Shoots of "APOLLO" emerge from winter dormancy approximately 1 week later than the commercial variety "Zeus" (non-patented) and I week earlier than the commercial variety "Galena" (non-patented). Emergence is typically late in March. Initial stem or shoot growth rate is moderate. After spring pruning, growth continues to be average when compared to other commercial varieties. The main vine stems are green (RHS 137C) with 6 faint purple (RHS N77B) stripes unlike "Zeus", which has distinct purple stripes. The main vine stems are hexagonal in cross-section shape. Inflorescence of "APOLLO" begins to appear in early July and mature during the second week of September. Cone shape is fairly uniform in the "APOLLO" variety. The hop cones of "APOLLO" are well adapted to mechanical harvest because of their compactness and ovoid shape. The cones do not shatter during harvest. In the following description color code designations are by reference to the RHS Colour Chart, $4^{th}$ Edition, provided by the Royal Horticultural Society of Great Britain.

4. Plant characteristics:
   - *Plant.*—Is made of up many parts and colors vigorous, climbing vine.
   - *Plant shape.*—Columnar to fusiform. Bine color green (RHS 137C).
   - *Bine stripe.*—Pink violet (RHS N77B).
   - *Bine inter-node length (at 6' high).*—20 cm.
   - *Bine diameter (at 6' high).*—1 cm.
   - *Bine length.*—18'.
   - *Petiole length.*—6–7 cm. Petiole color green (RHS 144A).
   - *Petiole shape.*—Slightly channeled (flat upper surface).
   - *Leaf arrangement.*—Opposite.
   - *Leaf shape.*—Cordate to palmate. Leaf color— upper surface— dark green— (RHS 137A). Leaf color— lower surface— green— (RHS 137C).
   - *Mature leaf width.*—13–15 cm.
   - *Mature leaf length.*—13–15 cm.
   - *Number of main bine leaf lobes.*—Five.
   - *Veination pattern.*—Reticulate.
   - *Vein color.*—Green (RHS 144A).
   - *Leaf margin.*—Moderately serrate to dentate. Lateral branch length (at 6' high)" 0.5–1.0 m. Internode length of lateral branch (at 6' high): 8–12 cm. Stipulate growth direction up-forked.
   - *Stipule color.*—Green (RHS 146C).
5. Reproductive organs, cones, cone parts, seeds:
   - *Bract color.*—(RHS 137C).
   - *Bract tips shape.*—Acuminate.
   - *Bract tip position.*—Mostly appressed, some bracts are slightly everted at full maturity.
   - *Bract diameter.*—1.2 cm.
   - *Bracteole shape.*—Lanceolate.
   - *Bracteole color.*—(RHS 145B).
   - *Compactness.*—Tight, very dense.
   - *Shape.*—Ovoid to cylidrical.
   - *Cone length.*—4 cm.
   - *Cone tip shape.*—Bluntly pointed.
   - *Cone weight.*—200–250 mg.
   - *Strig.*—Compact.
   - *Lupulin glands.*—The cone of the present variety contains numerous lupulin glands.
   - *Yield per acre.*—2900–3350 pounds on average. However, this yield is contingent upon temperature, soil conditions and cultural practices, and is therefore not distinctive of the present variety.
   - *Seeds.*—Highly variable in size and color depending on male parent.
   - *Date of maturity.*—Considered to be middle (Sept. 5–Sept. 20) as compared to other common hop varieties grown in central Washington.
6. Analytical data of cones:
   - % *Alpha-acids (bale).*—15.0–19.0% (ASBC Spectrophotometric method).
   - % *Beta-acids (bale).*—5.5–8.0% (ASBC Spectrophotometric method).
   - *Alpha/beta ratio.*—3.0–3.5.
   - *Cohumulone (% of alpha-acids).*—24–28%.
   - *Colupulone (% of beta-acids).*—52%.
   - *Storage characteristics.*—15% transformation of alpha acids after 6 months at 22° C.
   - *Total oils (mls/100 g).*—1.5–2.5.
   - *Humulene (% of total oils).*—20–35%.
   - *Caryophyllene (% of total oils).*—14–20%.
   - *Humulene/caryophyllene ratio.*—1.9.
   - *Farnesene (% of total oils).*—0%.
   - *Myrcene (% of total oils).*—30–55%.
7. Disease resistance: The variety "APOLLO" is resistant to the strains of powdery mildew fungus found in the Yakima valley as of 2005, but since not all strains are present no future powdery mildew resistance can be assured. "APOLLO" appears to be tolerant to strains of Verticillium wilt and the virus diseases found in the USA growing areas. Tolerance to hop downy mildew fungus is very good and preventative measures are not necessary in the Yakima Valley growing region. Tolerance to the major soil borne pests and diseases, such as Phytophthora root rot is not known at this time.

8. Regional adaptation: The "APOLLO" variety is well adapted to the drier growing regions of Washington State, specifically the Yakima Valley. "APOLLO" has not been tested in other growing locations.
9. Ploidy: Hop variety "APOLLO" is diploid. The mother is diploid and the father is diploid.
10. Life expectancy: Indefinite similar to other hop varieties.
11. Use: Flavoring and conditioning of beverages and foods and use as a vegetable. Constituent of herbal remedies, nutraceuticals, pharmaceuticals, drugs, ointments, antiseptic washes and cosmetics for humans and animals. Constituent of fodder, bedding, compost, agricultural treatments, phytoremediation treatments, water and soil treatments, conditioning of fermentation and other industrial processes. Used in breeding novel hop varieties.
12. Propagation status: "APOLLO" rootstock and plant propagation material exists. Asexual plant propagation has been demonstrated.
13. Reproductive status: "APOLLO" is fertile and produces seeds upon pollination with male hop plants.

DISTINGUISHING CHARACTERISTICS

This new hop variety "APOLLO" can be distinguished from all other USA commercial varieties by its resistance to powdery mildew in combination with a very high percentage of alpha-acids, low CoH, and excellent yield. There are currently no commercial varieties grown in the USA exhibiting complete powdery mildew resistance and providing a high alpha-acid yield.

We claim:

1. A new and distinct hop plant named "APOLLO", as herein described and illustrated.

* * * * *